United States Patent
Wiegert et al.

(10) Patent No.: US 8,712,121 B2
(45) Date of Patent: Apr. 29, 2014

(54) IMAGE GENERATION DEVICE WITH OPTIMIZED DOSE CONTROL

(75) Inventors: Jens Wiegert, Aachen (DE); Matthias Bertram, Aachen (DE)

(73) Assignee: Koninklijke Philips N.V., Eindhoven (NL)

( * ) Notice: Subject to any disclaimer, the term of this patent is extended or adjusted under 35 U.S.C. 154(b) by 356 days.

(21) Appl. No.: 13/000,030

(22) PCT Filed: Jun. 23, 2009

(86) PCT No.: PCT/IB2009/052686
§ 371 (c)(1), (2), (4) Date: Dec. 20, 2010

(87) PCT Pub. No.: WO2009/156943
PCT Pub. Date: Dec. 30, 2009

(65) Prior Publication Data
US 2011/0110573 A1    May 12, 2011

(30) Foreign Application Priority Data
Jun. 25, 2008  (EP) .................................... 08159000

(51) Int. Cl.
*G06K 9/00* (2006.01)
(52) U.S. Cl.
USPC .............................................. 382/128; 378/4
(58) Field of Classification Search
USPC ................. 382/100, 128, 139, 130, 131, 132; 128/922; 378/4–27, 51, 62, 64, 70; 250/370.01, 370.07–370.09
See application file for complete search history.

(56) References Cited

U.S. PATENT DOCUMENTS

| | | | |
|---|---|---|---|
| 5,379,333 A | 1/1995 | Toth | |
| 5,396,531 A * | 3/1995 | Hartley | 378/108 |
| 5,400,378 A * | 3/1995 | Toth | 378/16 |
| 6,493,416 B1 | 12/2002 | Hsieh | |
| 6,744,846 B2 * | 6/2004 | Popescu et al. | 378/16 |
| 2004/0062341 A1 * | 4/2004 | Popescu et al. | 378/4 |
| 2007/0147579 A1 * | 6/2007 | De Man et al. | 378/16 |
| 2007/0189444 A1 * | 8/2007 | Van Steven-Daal et al. | 378/6 |
| 2009/0274272 A1 * | 11/2009 | Stanton et al. | 378/62 |

FOREIGN PATENT DOCUMENTS

EP   1172069 A1   1/2002

OTHER PUBLICATIONS

Kalender et al: "Technical Approaches to the Optimisation of CT"; Physics Medica, 2008, vol. 24, pp. 71-79.

* cited by examiner

*Primary Examiner* — Anand Bhatnagar

(57) ABSTRACT

The present invention relates to an image generation device for generating an image from measured data, wherein image quality is optimized for a region of interest and to an imaging system comprising this image generation device. The image generation device comprises a noise determination unit for determining a distribution of noise in a projection domain of the region of interest, and a dose control unit (32) for determining a dose profile for a radiation source (2) of said image generation device based on said determined distribution of noise by using a noise propagation algorithm. Thereby, signal-to-noise ratio of a reconstructed volume can be improved and is not sensitively dependent on a selected region of interest.

21 Claims, 3 Drawing Sheets

IMAGE GENERATION DEVICE WITH OPTIMIZED DOSE CONTROL

FIELD OF THE INVENTION

The present invention relates to an image generation device, an image generation method and a computer program for generating an image from measured data, wherein image quality is optimized for a region of interest. The invention relates further to an imaging system comprising the image generation device and a corresponding imaging method and computer program.

BACKGROUND OF THE INVENTION

Volumetric imaging capabilities, such as computed tomography (CT), interventional CT, CT fluoroscopy, 3D vascular imaging, etc., have become increasingly valuable tools over the past decades and years. X-ray CT is a technique which determines the internal make-up of an object by passing X-rays through the object and measuring the attenuation of the X-rays passing through the object. In this technique the object is sub-divided into many voxels, a voxel being a basic volumetric unit for imaging purposes. The number of radiological procedures using X-ray based volumetric imaging techniques has risen accordingly. However, these techniques account for a large fraction of the collective applied dose in radiology and therefore, the applied patient dose has become a critical issue. In order to combat the ever increasing patient dose, efficient dose saving techniques are required.

EP 1 172 069 A1 discloses CT with dose optimization by setting an optimized tube current in real time (automatic exposure control), a tube current modulation (dose minimization), and based thereon a post processing by an adaptive 3D filter (noise reduction). Dose profiles used for acquisition of projection data are calculated based on measured attenuation in the center of a detector. For reconstructed data this leads to a distribution of voxel-noise in such a way that the noise in the center of the reconstructed object is optimal. Even though this technique has found broad acceptance in CT the procedure is suboptimal for several reasons. As a first reason, using only the measured attenuation as a basis for the estimation of the contribution of the individual projection to the total noise in the reconstructed volume is only approximative. Spectral effects originating e.g. from beam hardening and the influence of scattered radiation are neglected. As a second reason, if scatter offset correction techniques are used prior to reconstruction, scattered radiation which represents a significant portion of the measured signal, as well as the impact of the scatter subtraction itself, need to be adequately accounted for in the calculation of the optimum dose profile. As a third reason, if a region other than the central region of the reconstructed volume is the region of interest (e.g., for cardiac CT) the optimum dose profile for the center of the reconstructed image and the region of interest may significantly differ. The dose profile for the center of the reconstructed volume may even decrease the contrast-to-noise ratio in the region-of-interest. It is therefore essential, to do the noise/dose optimization specific for the region of interest.

SUMMARY OF THE INVENTION

It is an object of the present invention to provide an image generation device, an image generation method and a computer program for generating an image from measured data, which provide enhanced dose control.

In a first aspect of the present invention an image generation device for generating an image from measured data, wherein image quality is optimized for a region of interest, is presented, wherein the image generation device comprises:
a noise determination unit for determining a distribution of noise in a projection domain of the region of interest; and
a dose control unit for determining a dose profile for a radiation source of said image generation device based on said determined distribution of noise by using a noise propagation algorithm.

The invention is based on the idea that noise is determined in individual voxels of the reconstructed volume on the basis of noise distributions in the projections. Using the projection noise distributions the optimum dose profile can be calculated on the basis of the noise propagation. The signal-to-noise ratio is specifically improved for the selected region of interest of the reconstructed volume. This solution offers multiple advantages including higher image quality by using the same dose, reduction of dose by maintaining image quality, and homogenization of noise induced artifact patterns, especially for asymmetric patient geometries.

In the noise propagation account can be taken of scatter of x-rays in the object as well as spectral effects such as beam hardening.

In a preferred embodiment, the region of interest may be specified by the user.

In another preferred embodiment, the region of interest may be selected by means of automatic or semi-automatic organ segmentation.

In a further embodiment, the dose profile can be determined based upon prior acquired projection data. In case of repeated acquisition with the same or similar geometry, the required information can be obtained from a previous scan.

In a further preferred embodiment, the dose profile can be determined based upon a model of the object comprising said region of interest. Thereby, pre-calculated data can be used for obtaining the dose profile.

In another preferred embodiment, the dose profile can be determined based upon a scout scan which is often used as a low-dose and/or low resolution scan in order to determine the FOV to be imaged.

In a still further embodiment, the noise propagation algorithm may specifically account for at least one of spectral effects (e.g. beam hardening) and scattered radiation.

It is preferred that the dose profile is determined based on at least one of a reduced spatial resolution lower than a final resolution of said image and a simplified noise propagation algorithm, to thereby speed up determination of the optimal dose modulation.

In a further aspect of the present invention an imaging system is presented, wherein the imaging system comprises:
a measured data generation unit for generating measured data of an image, and
an image generation device for generating said image from the measured data as defined in claim 1.

In a further aspect of the present invention an image generation method for generating an image from measured data is presented, wherein image quality is optimized for a region of interest and wherein the image generation method comprises following steps:
determining a distribution of noise in a projection domain of the region of interest; and
determining a dose profile for a radiation based on said determined distribution of noise by using a noise propagation algorithm.

In a further aspect of the present invention an imaging method comprising following steps:

generating measured data by a measured data generation unit, and generating an image from the measured data according to the steps as defined in claim 1 by an image generation device.

In a further aspect of the present invention a computer program for generating an image from measured data is presented, wherein the computer program comprises program code means for causing an image generation device as defined in claim 1 to carry out the steps of the detection method as defined in claim 11, when the computer program is run on a computer controlling the image generation device.

In a further aspect of the present invention a computer program for imaging is presented, wherein the computer program comprises program code means for causing an imaging system as defined in claim 10 to carry out the steps of the imaging method as defined in claim 12, when the computer program is run on a computer controlling the imaging system.

It shall be understood that the image generation device, the imaging system, the imaging generation method, the imaging method and the computer programs have similar and/or identical preferred embodiments as defined in the dependent claims.

It shall be understood that a preferred embodiment of the invention can also be any combination of the dependent claims with the respective independent claim.

BRIEF DESCRIPTION OF THE DRAWINGS

These and other aspects of the invention will be apparent from and elucidated with reference to the embodiment(s) described hereinafter. In the following drawings.

DETAILED DESCRIPTION OF EMBODIMENTS

Figure 1:
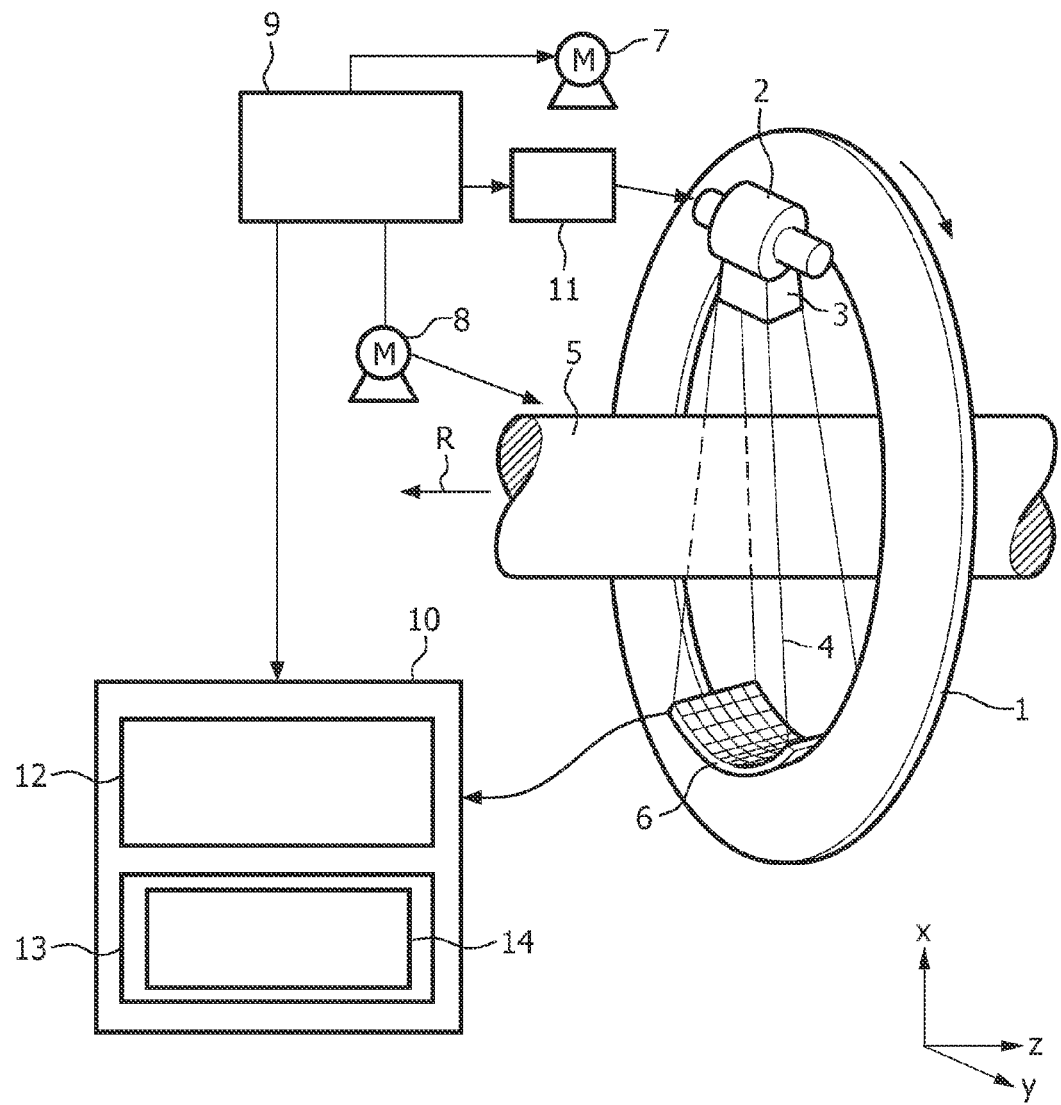
FIG. 1 shows schematically and exemplarily a representation of an imaging system for imaging a region of interest comprising enhanced dose control in accordance with the invention.

FIG. 1 shows schematically and exemplarily an imaging system being a computed tomography system. The computed tomography system includes a gantry 1 which is capable of rotation about a rotational axis R which extends parallel to the z direction. A radiation source 2, which is, in this embodiment, an X-ray tube, is mounted on the gantry 1. The radiation source 2 is provided with a collimator 3, which forms, in this embodiment, a conical radiation beam 4 from the radiation generated by the radiation source 2. The radiation traverses an object (not shown), such as a patient, and a region of interest (ROI), which is preferentially located within the object, in an examination zone, which is, in this embodiment, cylindrical. After having traversed the examination zone 5 the radiation beam 4 is incident on a detection device 6, which comprises a two-dimensional detection surface. The detection device 6 is mounted on the gantry 1. The computed tomography system may be adapted to generate a "normal" computed tomography scan with data not only measured for the region of interest but for the entire patient, while dose control is performed in such a way that the image quality is optimal for a (user specified) ROI within the reconstructed image comprising the entire patient (and not only the ROI).

The computed tomography system comprises two motors 7, 8. The gantry 1 is driven at a preferably constant but adjustable angular speed by the motor 7. The motor 8 is provided for displacing the object, for example, a patient, who is arranged on a patient table in the examination zone 5, parallel to the direction of the rotational axis R or the z axis. These motors 7, 8 are controlled by a control unit 9, for instance, such that the radiation source and the examination zone 5 and, thus, the regions of interest within the examination zone move relatively to each other along a helical trajectory. However, it is also possible that the object or the examination zone 5 is not moved, but that only the radiation source 2 is rotated, i.e. that the radiation source moves along a circular trajectory relative to the object or the examination zone 5. Furthermore, in another embodiment, the collimator 3 can be adapted for forming another beam shape, in particular a fan beam, and the detection device 6 can comprise a detection surface, which is shaped corresponding to the other beam shape, in particular to the fan beam.

During a relative movement of the radiation source and the examination zone 5 the detection device 6 generates measured values depending on the radiation incident on the detection surface of the detection device 6. Therefore, the radiation source 2, the elements for moving the radiation source 2 relative to the examination zone, in particular, the motors 7, 8 and the gantry 1, and the detection device 6 form a measured data generation unit for generating measured data.

The measured data, which are, in this embodiment, projection data, are provided to an image generation and display device 10 for generating and displaying an image comprising the region of interest from the measured data, i.e. from the projection data. The region of interest is located within the examination zone and preferentially contains an object or a part of an object. The image generation and display device 10 comprises an image generation unit 12 for generating and processing an image from the measured data and an image display unit 13 with a display screen 14 for displaying the generated image.

Also the image generation and display device 10 may preferably be controlled by the control unit 9. In another embodiment, the control unit 9 can also perform the control of the image generation unit 12 or parts thereof.

Additionally, a dose modulation unit 11 (e.g. a dose modulation processor or the like) is provided, which controls or communicates with a power supply (not shown) of the radiation source 2 so as to control the radiation intensity generated by the radiation source 2 during tomographic imaging. In the illustrated embodiment, the radiation source 2 is an x-ray tube and the dose modulation unit 11 may be adapted to control the x-ray tube filament or cathode current to modulate the x-ray intensity generated by the radiation source 2. In other contemplated embodiments, dose modulation of the dose modulation unit 11 may be produced by shuttering or filtering the radiation beam, by modulating the tube voltage, by modulating the electrical bias on a Wehnelt cylinder, or so forth.

The dose modulation of the dose modulation unit 11 generally reduces the radiation intensity generated by the radiation source 2 when acquiring tomographic imaging data in the region of interest.

The basic procedure of the invention in all its embodiments employs a noise propagation model that allows for spatially resolved computation of the voxel noise in reconstructed images based on the noise distributions found in projection data. In particular it allows to accurately compute the noise contributions originating from each individual projection direction. Using these noise contributions from each projection direction the proposed procedure allows to compute desired dose/tube current profiles for achieving improved image quality in terms of contrast-to-noise ratio for user-selected region of interest (ROI), i.e. at any selected position in the reconstructable field of view (FOV).

Providing either a scatter model or a scatter estimation procedure, the procedure or algorithm can explicitly take into account the impact of scattered radiation, further increasing the dose efficiency over current attenuation based methods.

Figure 2:
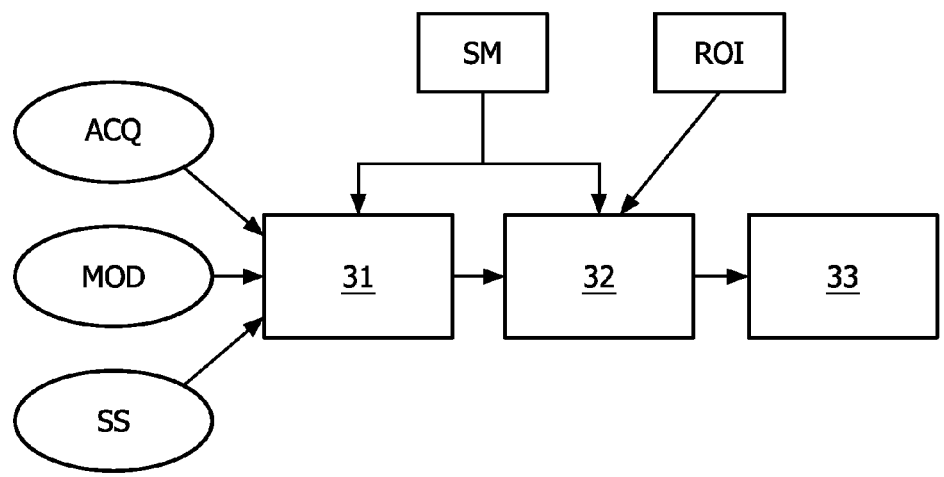
FIG. 2 shows dose control processing in accordance with an embodiment of the invention.

FIG. 2 shows a block diagram of an example of the proposed dose optimization processing which may be performed in the control unit 9 or an additional separate dose control unit or processor (not shown) to control the dose modulation unit 11. In a first control stage 31, the expected distribution of noise in the projection domain is determined, which is called "projection noise distribution". This may be achieved by different alternative approaches, e.g., the expected noise distribution could be obtained based upon prior acquired projection data ACQ, upon a patient model MOD, or upon a scout scan SS. These alternative approaches could be applied solely or in combination. Using the obtained projection noise distribution the optimum dose profile can be calculated in a second control stage 32 using a noise propagation algorithm. Both for the determination or calculation of the noise distribution in the projections and for the noise propagation algorithm, the amount of scattered radiation contained in the projections can be taken into account based on a scatter model SM or scatter estimation algorithm. The optimum noise distribution is calculated specifically for a user-selectable position or ROI in the volume to be reconstructed. Finally, in a third control stage 33 the optimum dose distribution (tube current profile) is passed to the dose modulation unit 11.

Figure 3:
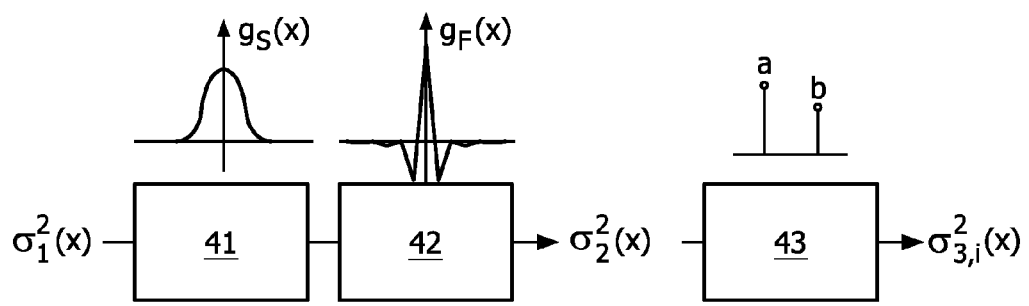
FIG. 3 shows processing for determination of noise contribution in accordance with the invention.

FIG. 3 shows a block diagram of a simplified imaging chain of a tomography system representing, e.g., a conventional CT system or a C-arm based flat-detector cone-beam CT system.

It can be generally shown by quadratic error propagation that an uncorrelated non-stationary noise distribution $\sigma_1^2(x)$ propagates through a linear shift-invariant system $g_G(x)$ as $$\sigma_2^2(x) = g_G^2(x) * \sigma_1^2(x) \tag{1}$$

Filtered backprojection type reconstruction algorithms can be interpreted as linear systems and, therefore, noise propagation through such kind of algorithms can be developed based on equation 1.

Typically, the imaging chain of such system comprises detector related image forming components 41, such as a detector point spread function (PSF), and projection based processing (binning, low-pass filtering (not shown)). Furthermore, the imaging chain comprises reconstruction algorithm related image forming components 42, like a reconstruction filter, and components 43 related to interpolation and backprojection.

For the example given in FIG. 3, the noise contribution $\sigma_{3,i}^2(x_j)$ of one projection i to the total noise of the reconstructed voxel j can be calculated as:

$$\sigma_{3,i}^2(x_j) = a_{ij}^2 \cdot (g_G^2 * \sigma_1^2)(x_{0,ij}) + b_{ij}^2 \cdot (g_G^2 * \sigma_1^2)(x_{0,ij}+1) + 2 \cdot a_{ij}^2 \cdot b_{ij}^2 \cdot ((g_G(x)g_G(x+1)) * \sigma_1^2(x))(x_{0,ij}) \tag{2}$$

In this equation $g_G(x)$ represent the joint transfer function $g_G(x)$ including the detector point spread function $g_S(x)$ and the transfer function of the reconstruction filter $g_F(x)$. For simplicity, for the interpolation step in equation 2 fan beam geometry (two interpolation weights) has been assumed, while an extension to the cone-beam case (generally four interpolation weights) is straight forward.

Figure 4:
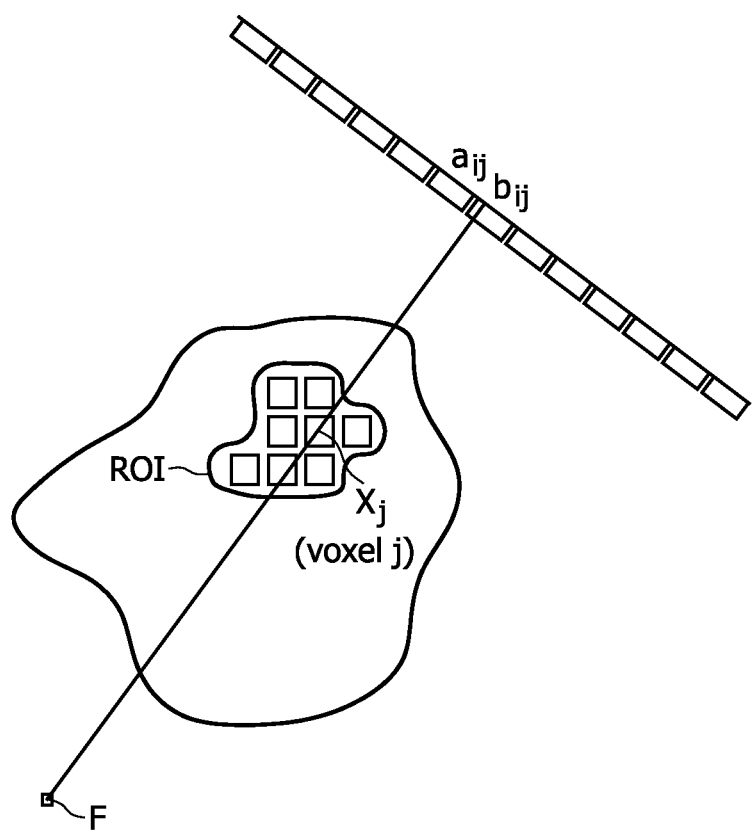
FIG. 4 illustrates geometry and nomenclature used in the invention.

FIG. 4 illustrates the geometry and nomenclature used here assuming fan beam geometry. For projection i, the ray from the focal spot F through the center of voxel j at the position $x_j$ determines the interpolation position on the detector and accordingly the interpolation weights $a_{ij}$ and $b_{ij}$.

Using equation 2, the noise variance contribution of each individual projection to the voxel j is computed. The total noise variance of the voxel j is computed by summing the individual contributions from all projections according to:

$$\sigma_3^2(x_j) = \sum_i \sigma_{3,i}^2(x_j) \tag{3}$$

A representative value for the voxel noise for an entire region-of-interest may be computed in linear manner by summing up all sigma values, or may as well be computed using a squared average, i.e. building a root mean square (RMS) value. The latter can be achieved as follows, for example. The RMS value as a measure for the voxel noise within a the ROI can be computed according to:

$$\sigma_{RMS}(ROI) = \sqrt{\frac{1}{N_j}\sum_j \sigma_3^2(x_j)} = \sqrt{\frac{1}{N_j}\sum_j \sum_i \sigma_{3,i}^2(x_j)} \tag{4}$$

In this way, large values ("noise" outliers) have a larger impact on the total noise and will thus have a stronger influence on the current modulation to be discussed in the following.

The average voxel noise in the region of interest a $\sigma_{RMS}$ (ROI) can be reduced by modulating the tube current at the radiation source 2 in such a way that for projections with large noise contributions the tube current is increased while for projections with little noise contributions a reduced tube current is used. As an optional constraint, the totally administered radiation can be kept constant.

Tube current modulation, e.g. by the dose modulation unit 11, can be incorporated in the above described embodiment by means of a relative tube current modulation factor $C_i$. The tube current of a projection is computed as $I_i = C_i \cdot I_{avg}$, where $I_{avg}$ is the average tube current used without modulation. Due to the tube current modulation factor the individual variance contributions are scaled with the reciprocal value of the modulation factor such that the voxel noise of one voxel is computed now $$\sigma_3^2(x_j) = \sum_i \frac{1}{C_i} \cdot \sigma_{3,i}^2(x_j). \tag{5}$$

Using the constraint $$\frac{1}{N_i}\sum_i C_i \stackrel{!}{=} 1 \tag{6}$$

the minimization task can then be defined by $$\sigma_{RMS}^2(ROI) = \frac{1}{N_j}\sum_i \frac{1}{C_i}\sum_j \sigma_{3,i}^2(x_j) = \sum_i \frac{1}{C_i}\sigma_{pro,i}^2 \stackrel{!}{=} \min. \tag{7}$$

In the above equation the contributions to the total a $\sigma_{RMS}^2$ (ROI) originating from each projection have been pooled in a single quantity $\sigma_{pro,i}^2$.

Using partial derivatives $$\frac{\partial}{\partial C_i}\sigma^2_{RMS}(ROI)$$

and the constraint defined by equation 6 the solution of the optimization task given in equation 7 is found for $$C_i = \frac{1}{\frac{1}{N_i}\sum_{i'}\sigma_{pro,i'}} \cdot \sigma_{pro,i} \qquad (8)$$

i.e. equation 8 defines the optimum relative tube current modulation factors.

Determination of noise propagation and calculation of optimal relative tube current modulation factors can be achieved based on a specification of the input noise variances $\sigma_1^2$. Since during propagation through the patient the polyenergetic beam spectrum is continuously changing, the measured energy-integrated detector signal may be not entirely proportional to the number of quanta reaching the detector. Since the number of quanta determines the quantum noise it is important to take the spectral changes into account, as can be gathered from equation 9 below.

Additionally, in order to account for the log-conversion involved in the reconstruction process from measured X-ray profiles, equation 9 contains a noise enhancement factor calculated by the reciprocal value of the normalized primary radiation $$\frac{1}{I_P}.$$

This factor represents the local slope of the logarithm function and can be derived by a $1^{st}$ order taylor expansion.

$$\sigma_1 = \frac{1}{I_P}\frac{\sqrt{\int n_P(E)\cdot E^2 dE}}{\int n_0(E)\cdot E dE} = \qquad (9)$$

$$\frac{1}{I_P}\frac{1}{\sqrt{N_0}}\frac{\sqrt{I_P \cdot \frac{\langle E_P^2\rangle}{\langle E_P\rangle}}}{\sqrt{\langle E_0\rangle}} = \frac{1}{I_P}\frac{1}{\sqrt{N_0}}\sigma_P(I_P, \text{spectrum})$$

In this equation, $n_P(E)$ and $n_0(E)$ are the spectral photon count rate densities impinging onto the detection device 6, $N_0$ is the number of photons reaching a detector cell without attenuation in the patient, $\langle E_P\rangle$ and $\langle E_0\rangle$ are mean energies of the spectrum prior and after attenuation in the patient and $\langle E_P^2\rangle$ is the mean squared energy of the spectrum after attenuation in the patient. For a practical implementation of equation 9, values for $\sigma_P(I_p, \text{spectrum})$ can be stored by means of a look-up table (LUT) or by means of parametric computation schemes.

If scatter offset correction techniques or measures are used prior to reconstruction, scattered radiation may be adequately accounted for. In presence of scattered radiation, the input noise can be computed analogously to equation 9 according to:

$$\sigma_1 = \qquad (10)$$
$$\frac{1}{I_P}\frac{1}{\sqrt{N_0}}\frac{\sqrt{I_P\cdot\frac{\langle E_P^2\rangle}{\langle E_P\rangle}+I_S\cdot\frac{\langle E_S^2\rangle}{\langle E_S\rangle}}}{\sqrt{\langle E_0\rangle}} = \frac{1}{I_P}\frac{1}{\sqrt{N_0}}\sigma_{PS}(I_P, I_S, \text{spectrum})$$

Also for this case, values for the function $\sigma_{PS}(I_P, I_S, \text{spectrum})$ may be a priori calculated and stored by means of a LUT or computed by a parametric model.

In presence of scattered radiation, $I_P$ and $I_S$ can be determined from the measured detector signal $I_{measured}=I_P+I_S$. This can be done by a simple scatter model or based on scatter estimation algorithms (e.g. the same algorithms as used for correcting the projection data intended for reconstruction).

It is noted that correctly accounting for the amount of scattered radiation found in the measured detector signal is advantageous for obtaining truly optimal dose modulation curves. Simply using attenuation based quantities in order to derive the input noise distributions as proposed by known techniques described in e.g. EP 1 172 069 A1 may lead to suboptimal results.

Dose calculation or determination can be accelerated by simplifying the above noise propagation formula. In case the function $g_G$ is of short lateral extent (similar to a delta peak), which is often the case in typical CT and flat-detector based cone-beam CT systems, the noise propagation formula can be approximated by:

$$\sigma_{3,i}^2(x_j)=a_{ij}^2\cdot G_{G0}^2\cdot\sigma_1^2(x_{0,ij})+b_{ij}^2\cdot G_{G0}^2\sigma_1^2(x_{0,ij}+1)+$$
$$a_{ij}^2\cdot b_{ij}^2\cdot G_{G1}^2\cdot(\sigma_1^2(x_{0,ij})+\sigma_1^2(x_{0,ij}+1)) \qquad (11)$$

using $$G_{G0}^2 = \sum_{x=-\infty}^{\infty}g_G^2(x) \text{ and } G_{G1}^2 = \sum_{x=-\infty}^{\infty}g_G(x)\cdot g_G(x+1)$$

such that no convolution filtering is required any more. $G_{G0}^2$ and $G_{G1}^2$, can be calculated a priori.

Then only those projection values corresponding to the projection of the ROI (in the extreme case only two detector cells per projection) need to be included in the calculation.

With proper scaling factors the noise propagation can be done using a much coarser spatial resolution than the finally intended reconstruction of the image data, largely reducing the amount of input data and accelerating the calculation of the optimal dose modulation.

In the following, various embodiments of the invention are described based on the alternative noise distribution sources indicated in FIG. 2.

In case of using the scout scan SS, for scan planning in CT often a low-dose low-resolution scout scan of the patient is performed in order to determine, e.g., the FOV to be imaged. Using this scout scan projection data and a user specified ROI within the reconstructable area the optimum dose profile can be computed using equations 2, 8 and 9, using a scatter correction algorithm and using low-resolution data for speed-up.

Using the patient model PM with parameters such as body size, body weight, imaging region, pre-calculated data can be used for the term $$\frac{1}{N_i} \sum_{i'} \sigma_{pro,i'}$$

in equation 8. Then, the optimum dose profile can be computed using equations 2, 8 and 10 where for computation of the tube values of an individual projection i input data from projection all so far acquired projections i-n (n=1 ... 10) may be used. In this case computation may be speed-up by using both reduced spatial resolution and the simplified noise propagation formula.

Using previous scan data ACQ in case of a repeated acquisition with the same geometry, the required information can be obtained from this previous scan. Then the same procedure as for the scout scan SS may be used.

In summary, an image generation device and method for generating an image from measured data have been described, wherein image quality is optimized for a region of interest and wherein a distribution of noise is determined in a projection domain of the region of interest, and a dose profile for a radiation source is determined based on the determined distribution of noise by using a noise propagation algorithm. Thereby, signal-to-noise ratio of a reconstructed volume can be improved specifically for a selected region of interest.

The proposed dose control procedures can be used both for application in helical and axial CT scanner as well as in flat-detector based cone-beam CT systems, such as three-dimensional rotational angiography (3DRA) or three-dimensional rotational X-ray (3DRX) products.

In the above embodiments, the imaging system is a computed tomography system, but in other embodiments, the imaging system can also be any other imaging modality, for example, a nuclear imaging system.

The invention can be used for generating an image of a living object, like a patient, but it can also be used for generating an image of a technical object.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or devices may fulfill the functions of several items recited in the claims. The mere fact that certain measures are recited in mutually different dependent claims does not indicate that a combination of these measures cannot be used to advantage.

The calculations and determinations and/or the control of the dose modulation in accordance with the above described procedures can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention claimed is:

1. An image generation device for generating an image from measured data generated by an imaging system, wherein the imaging system includes a radiation source and a power supply for the radiation source, and wherein an image quality of the image is optimized for a region of interest in the image, the image generation device comprising:
   a noise determination unit that determines, in a projection domain, an expected distribution of noise of individual projections of second data for the region of interest;
   a dose control unit that determines a dose profile for the region of interest based on said determined distribution of noise of the individual projections using a noise propagation algorithm;
   wherein the dose control unit controls the power supply based on the dose profile so as to control a radiation intensity generated by the radiation source during tomographic imaging, with the imaging system, that generates the measured data; and
   an image generation unit that processes the measured data and generates the image from the measured data.

2. The image generation device as claimed in claim 1, wherein said region of interest is specified by the user.

3. The image generation device as claimed in claim 1, wherein said region of interest is selected by means of automatic or semi-automatic organ segmentation.

4. The image generation device as claimed in claim 1, wherein said second data is a model of an object comprising said region of interest.

5. The image generation device as claimed in claim 1, wherein said secton data is a scout scan.

6. The image generation device as claimed in claim 5, wherein said second data is obtained by a scanning operation with at least one of low-dose and low-resolution.

7. The image generation device as claimed in claim 1, wherein said noise propagation algorithm accounts for at least one of spectral effects and scattered radiation.

8. The image generation device as claimed in claim 1, wherein said noise determination unit determines said noise distribution based on at least one of a reduced spatial resolution lower than a final resolution of said image and a simplified noise propagation algorithm.

9. The image generation device as claimed in claim 1, wherein the dose control unit controls an x-ray tube cathode filament current to modulate that x-ray intensity generated by the radiation source during the tomographic imaging.

10. The image generation device as claimed in claim 1, wherein the noise determination unit determines the noise distribution based on prior acquired projection data.

11. The image generation device as claimed in claim 1, wherein the expected distribution of noise is determined at least in part by summing the individual projections of the second data.

12. The image generation device as claimed in claim 1, wherein the dose control unit further determines a tube current of each individual projection based on the product of a relative tube current modulation factor and an average tube current without modulation.

13. The image generation device as claimed in claim 12, wherein the noise determination unit determines individual variance contributions by scaling the distribution of noise by the reciprocal of the relative tube current modulation factor.

14. An imaging system comprising:
   a radiation source. which is powered by a power;
   a power supply that supplies the power to the radiation source;
   a noise determination unit that determines an expected distribution of noise, in a projection domain, of ndividual projections of second data for a region of interest in a volume to be reconstructed;

a dose control unit that determines a dose profile for the region of interest based on the determined distribution of noise of the individual projections using a noise propagation algorithm;

a dose modulation processor that controls the power supply based on the dose profile so as to control a radiation intensity generated by the radiation source during tomographic imaging that generates measured data;

a measured data generation unit that generates the measured data; and an image generation device that generates said image from the measured data.

15. An image generation method for generating an image from measured data, wherein image quality is optimized for a region of interest, the image generation method comprises following steps:

determining an expected distribution of noise of individual projections of the measured data, in a projection domain, of the region of interest;

determining a dose profile for the region of interest based on said determined distribution of noise of the individual projections of the measured data by using a noise propagation algorithm;

Controlling, based on the dose profile, a radiation intensity generated during tomogrphic imaging that generates the measured data; and processing the measured data to generate the image from the measured data.

16. An imaging method comprising following steps:

generating measured data by a measured data generation unit, and generating an image from the measured data according to the steps as defined in claim 15 by an image generation device.

17. The image generation method as claimed in claim 15, wherein the noise determination is based on prior acquired projection data.

18. The method as claimed in claim 15, wherein the distribution of noise is further based on the summation of the individual projections of the second data.

19. The method as claimed in claim 15, further comprising determining a tube current of a projection based on the product of a relative tube current modulation factor and an average tube current without modulation.

20. The method as claimed in claim 19, further comprising determining individual variance contributions by scaling the distribution of noise by the reciprocal value of the relative tube current modulation factor.

21. A computer program stored on a non-transitory medium for generating an image from measured data, the computer program comprising program code means for causing an image generation device comprising a noise determination unit for determining a distribution of noise in a projection domain of the region of interest; and a dose control unit for determining a dose profile for a radiation source of said image generation device based on said determined distribution of noise by using a noise propagation algorithm to carry out the steps of the detection method as defined in claim 15, when the computer program is run on a computer controlling the image generation device.

* * * * *